United States Patent [19]
Murphy

[11] Patent Number: 6,020,918
[45] Date of Patent: Feb. 1, 2000

[54] PIPE INSPECTION APPARATUS

[76] Inventor: Patrick M. Murphy, 312 rockwood Dr., Painesville, Ohio 44077

[21] Appl. No.: 08/883,422

[22] Filed: Jun. 26, 1997

[51] Int. Cl.[7] ...................................................... H04N 7/18
[52] U.S. Cl. .................................. 348/84; 354/63; 108/93
[58] Field of Search ................................ 348/84; 354/63, 354/219; 108/93; 33/178; 346/33

[56] References Cited

U.S. PATENT DOCUMENTS

| | | | |
|---|---|---|---|
| 3,964,171 | 6/1976 | Gambini et al. | 33/178 |
| 4,644,875 | 2/1987 | Watt | 108/93 |
| 4,985,032 | 1/1991 | Goble | 606/96 |
| 5,040,267 | 8/1991 | Dallmann | 16/239 |
| 5,287,133 | 2/1994 | Bohley . | |
| 5,359,939 | 11/1994 | Watt | 104/138.2 |
| 5,481,984 | 1/1996 | Oda et al. | 104/284 |

*Primary Examiner*—Bryan Tung
*Assistant Examiner*—Shawn S. An
*Attorney, Agent, or Firm*—Hill & Simpson

[57] ABSTRACT

An improved apparatus for inspecting and video taping pipelines is provided. A tubular vessel accommodates a video camera. A plurality of scuba lights are adjustably mounted to the periphery of the tubular housing at the front end of the apparatus. A dual-section guide leg is provided which has limited upward and downward movement and limited forward and rearward movement. An elastic member controls the upward/downward and forward/rearward movement of the guide leg to provide a shock absorber system. The guide leg engages the top inside surface of the pipeline as the apparatus is carried down the pipeline by the current. The angle of inclination of the apparatus may be controlled with weights, foam and the position of the guide leg.

15 Claims, 4 Drawing Sheets

PIPE INSPECTION APPARATUS

BACKGROUND OF THE INVENTION

The present invention relates to a new and improved pipe inspection apparatus and, more specifically, to an apparatus for recording video images of a pipeline interior. Water pipelines including those pipelines disposed underwater need periodic maintenance. In order to determine whether periodic maintenance is required, the pipes must be inspected. If the pipes are large enough, a diver can manually inspect the pipes for signs of wear and tear or rupture. However, inspecting pipes in this manual way is costly in terms of labor costs and is dangerous. Further, many pipelines are too long to be inspected manually, i.e. either the pipes are too long for a diver to physically swim the length of pipe required or, a diver is unable to carry a sufficient amount of oxygen to swim the length of pipe required.

As a result, automated apparatuses have been developed for the inspection of pipes. In a typical design, an apparatus equipped with a camera is tethered to a motor-driven winch and is dragged along the length of the pipeline. Because typical winches include only 12,000 feet of line, the tethered devices are limited to pipelines of about 2 miles in length. Because some pipelines are several miles in length, conventional tethered devices cannot be utilized. In addition to tethered devices, motor driven devices have been provided but these devices are limited by their battery life and therefore the length of pipeline that can be inspected using these devices is also limited.

As an improvement to the tethered and motor-driven devices, apparatuses have been developed which are carried along the length of the pipeline by the flowing fluid. One example of such a device is found in U.S. Pat. No. 5,287,133. In the device shown in this patent, a buoyant vessel is provided which carries a video camera. A supporting leg is mounted to the vessel in an off-center position and a wheel mounted on a lower end of the leg, rolls along the bottom surface of the pipe. The problems with the device shown and described in U.S. Pat. No. 5,287,133 are twofold. First, the guiding leg engages the bottom of the pipeline which typically contains more debris than the top surface of the pipeline. Because the leg engages more debris, the vessel and camera are shaken more thereby resulting in a video picture of a reduced quality. Further, while the device illustrated in U.S. Pat. No. 5,287,133 does provide some shock absorbing quality between the supporting leg and the vessel, the shock absorbing capability is limited. Still further, it is difficult to adjust the orientation or angle of the vessel with respect to the pipeline.

Accordingly, there is a need for an improved apparatus for inspecting pipeline by way of recording images of the interior of the pipeline with a video camera which provides for improved stability of the apparatus and the camera and improved adjustability of the angle of the apparatus and camera with respect to the pipeline interior.

SUMMARY OF THE INVENTION

The present invention satisfies the aforenoted need by providing an apparatus for inspecting pipe interior that includes a tubular housing with an interior in which a forwardly directed video camera is mounted. The housing has a front end through which the camera is directed and to which at least one light is mounted. In an embodiment, a plurality of lights are mounted about the front end of the housing. The housing includes an exterior to which a guide leg is mounted. More specifically, the guide leg includes a first section and a second section. The first section is pivotally mounted to the exterior of the housing at a midpoint thereof. The first section extends rearwardly along the housing which includes a slot disposed at the rear end of the housing so that the first section of the guide leg can pivot downward through the slot in the housing. However, a guide is provided at the housing which limits both the upward pivotal movement and the downward pivotal movement of the first section of the guide leg.

The first section of the guide leg includes a distal end which is pivotally connected to a second section of the guide leg. The second section of the guide leg extends upwardly and rearwardly from the rear end of the housing and a distal end of the second section of the guide leg engages the top of the pipeline as the apparatus floats down the pipeline with the current.

The second section of the guide leg is connected to the first section of the guide leg for limited pivotal movement with respect to the first section of the guide leg. More specifically, in an embodiment, the distal end of the first section of the guide leg includes two spaced apart parallel walls. A proximal end of the second section of the guide leg is disposed between the two walls and pivotally connected thereto by a pin or bolt. To limit the pivotal movement of the second section of the guide leg with respect to the first section of the guide leg, stop pins are provided in front of and behind the second section of the guide leg. The front stop pin limits the forward pivotal movement of the second section of the guide leg; the rear stop pin limits the rearward pivotal movement of the second section of the guide leg.

In an embodiment, a shock absorbing mechanism is provided by an elastic member that is connected to and stretches between the first section and second section of the guide leg. The guide through which the first section of the guide leg passes and the front stop pin are disposed between the points where the elastic member is connected to the first and second sections of the guide leg. As a result, the elastic member engages the guide and biases the first section of the guide leg in an upward position against an upper portion of the guide. Further, the elastic member also pulls the second section of the guide leg forward thereby biasing the second section of the guide leg against the front stop pin. However, downward movement of the front section of the guide leg is permitted as is rearward movement of the second section of the guide leg. The elastic member simply returns both legs to their biased position and therefore provides shock absorbing protection in both the up and down direction as well as the front-to-rear direction.

In an embodiment, the lights are attached to the exterior of the housing with adjustable brackets. Specifically, the brackets include a base member that is mounted to the housing and a bottom leg comprising two spaced-apart walls that extends along the length of the base. An inside leg is pivotally attached to one end of the outside leg between the spaced apart walls thereby permitting pivotal movement of the inside leg with respect to the outside leg. The lights are fastened to the inside leg with a tongue-in-groove connection. To secure the lights in place during use of the apparatus, nylon ties may be provided. Further, a nylon tie may be provided to lock the "on" switch to the light in the on position thereby preventing the light from being accidentally turned off during use.

In an embodiment, a sonic locator device may be attached to the housing of the apparatus which assists in the location of the apparatus in the event the apparatus becomes trapped or otherwise stuck during use.

In an embodiment, a cover for the front end of the apparatus may be provided for purposes of protecting the camera against protruding sticks, branches or pieces of re-bar.

In an embodiment, a plurality of weight compartments may be provided at the front end and at the rear end of the apparatus for adjusting the buoyancy of the apparatus.

In an embodiment, a plurality of foam sections may be provided at both the front end and at the rear end of the apparatus for adjusting the buoyancy of the apparatus.

In an embodiment, an improved method of inspecting the insides of pipelines is provided by introducing an apparatus made in accordance with the present invention inside a pipeline, activating the video camera of the apparatus, permitting the apparatus to float down the pipeline with the current and recording pictures of the interior of the pipeline as the apparatus is carried through the pipeline.

It is therefore an advantage of the present invention to provide an improved apparatus for the inspection of pipeline that travels through the pipeline in a smoother fashion than prior art apparatuses which results in a smoother video picture.

Another advantage of the present invention is to provide an apparatus for the inspection of pipeline which is more accurately adjustable in terms of the angle of inclination of the apparatus with respect to the pipeline axis.

Still another advantage of the present invention is to provide an apparatus for the inspection of pipeline interiors with improved shock absorbing capabilities.

Yet another advantage of the present invention is to provide an improved apparatus for the inspection of pipeline interiors with improved adjustable lighting.

Still another advantage of the present invention is to provide an improved apparatus for the inspection of pipeline interiors with improved buoyancy regulation.

Yet another advantage of the present invention is that it provides an apparatus for the inspection and videotaping of pipeline interiors that rides along the top wall of the pipeline.

Other objects and advantages of the invention will become apparent upon reading the following detailed description and appended claims, and upon reference to the accompanying drawings.

BRIEF DESCRIPTION OF THE DRAWINGS

For a more complete understanding of this invention, reference should now be made to the embodiments illustrated in greater detail in the accompanying drawings and described below by way of an example of the invention.

In the drawings.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE PRESENTLY PREFERRED EMBODIMENTS

Figure 1:
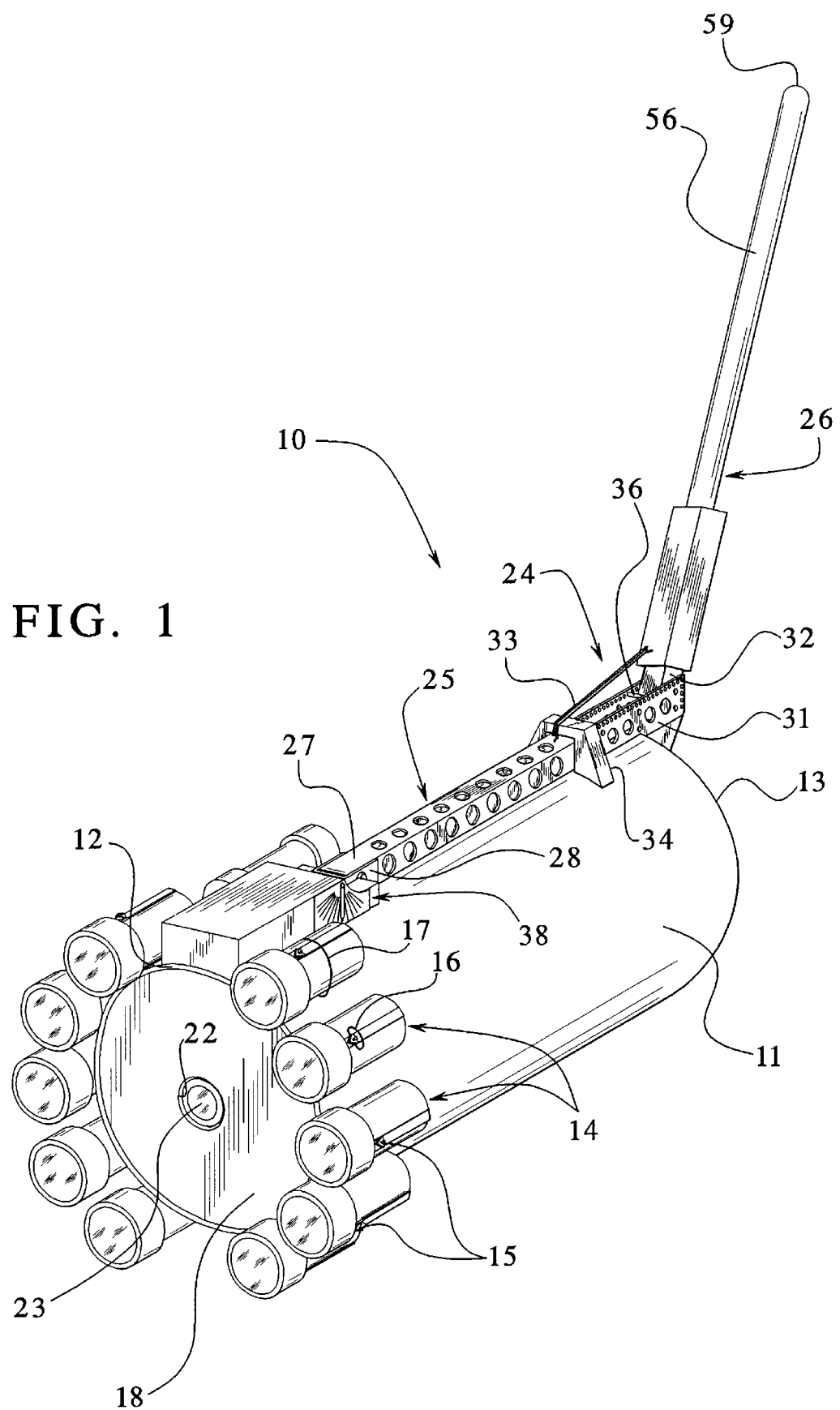
FIG. 1 is a perspective view of a pipeline inspecting apparatus made in accordance with the present invention.

Turning first to FIG. 1, an apparatus 10 made in accordance with the present invention is illustrated. The apparatus 10 includes a tubular housing 11 which includes a front end 12 and a rear end 13. The front end 12 includes a plurality of lights, shown generally at 14, each of which are battery operated and include their own on-off switch 15. To insure that the on-off switch 15 is maintained in the on position during use, a tie, one of which is shown at 16, may be employed to prevent the turning of the on-off switch 15 off during use. Further, an additional tie, one of which is shown at 17, may be used to hold the lights 14 in place on the respective brackets which are described in detail below with respect to FIG. 7.

Returning to FIG. 1, the front end 12 of the housing 11 accommodates a protective cover 18 which shields the video camera 21 (see FIG. 4) from damage during use. An aperture 22 in the cover 18 provides access to the lens 23.

Still referring to FIG. 1, a guide leg 24 is provided which includes a first section 25 and a second section 26. A proximal end 27 of the first section 25 of the guide leg 24 is mounted to the exterior of the housing 11 at the bracket 28. A distal end 31 of the first section 25 is pivotally connected to a proximal end 32 of the second section 26. An elastic member 33 is connected to the first section 25 and the second section 26 and provides a shock absorbing feature as discussed below. The first section 25 of the guide leg 24 passes through a guide 34 which limits the upward pivotal movement of the first section 25 of the guide leg 24. In addition, a lower guide 35 is provided to limit the downward pivotal movement of the first section 25 of the guide leg 24 (see FIG. 2).

Figure 2:
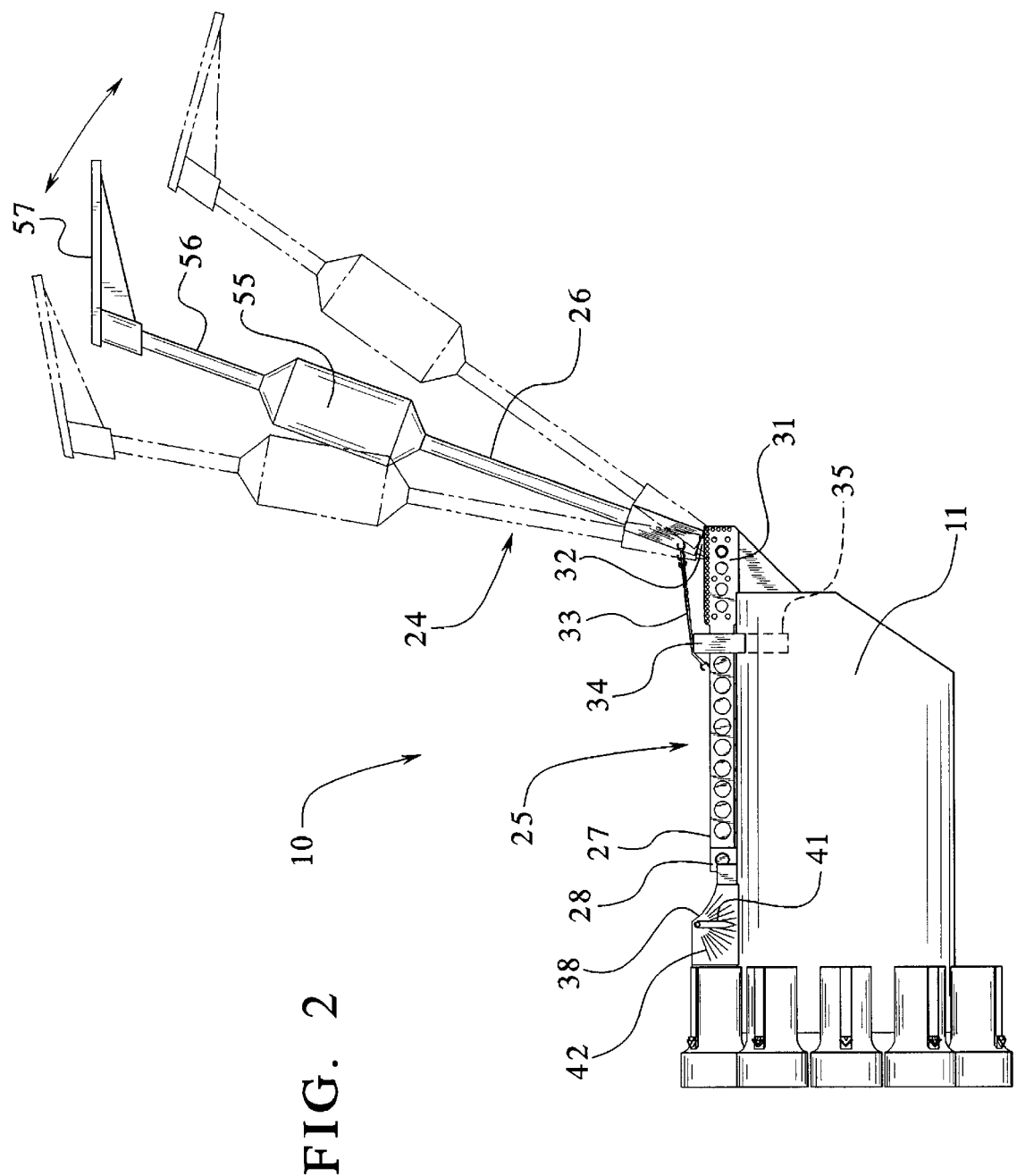
FIG. 2 is a side view of the apparatus shown in FIG. 1.

Referring to FIG. 2, as noted above, the first section 25 of the guide leg 24 is attached to the housing 11 at the bracket 28. This attachment is a pivotal attachment which permits the first section 25 to pivot upward and downward to an extent that is limited by the upper guide 34 and lower guide 35. The distal end 31 of the first section 25 is pivotally attached to the proximal end 32 of the second section 26. Again, this connection is pivotal but to an extent limited by the front stop pin 36 (see FIG. 1) and the rear stop pin 37 (see FIG. 5). Returning to FIG. 2, it will be noted that the elastic member 33 biases the second section 25 forward to an extent limited by the front stop pin 36. Further, the elastic member 33 biases the first section 25 upward to the extent limited by the upper brace 34. However, as shown in phantom in FIG. 3, downward movement of the first section 25 is possible and, as shown in phantom in FIG. 2, rearward movement of the second section 26 is possible but, as discussed above, is limited by the placement of the second stop pin and by the elastic member 33. If the weight of the second section 26 and the first section 25 is sufficient to overcome a biasing effect of the elastic member 33, the elastic member 33 will not bias the first section 25 snugly against the upper brace 34 or the second section 26 firmly against the first stop pin 36 and the guide leg 24 will assume the position shown in solid lines in FIG. 2 thereby permitting additional forward movement of the second section 26 as shown in the forward phantom view shown in FIG. 2.

Figures 3, 4:
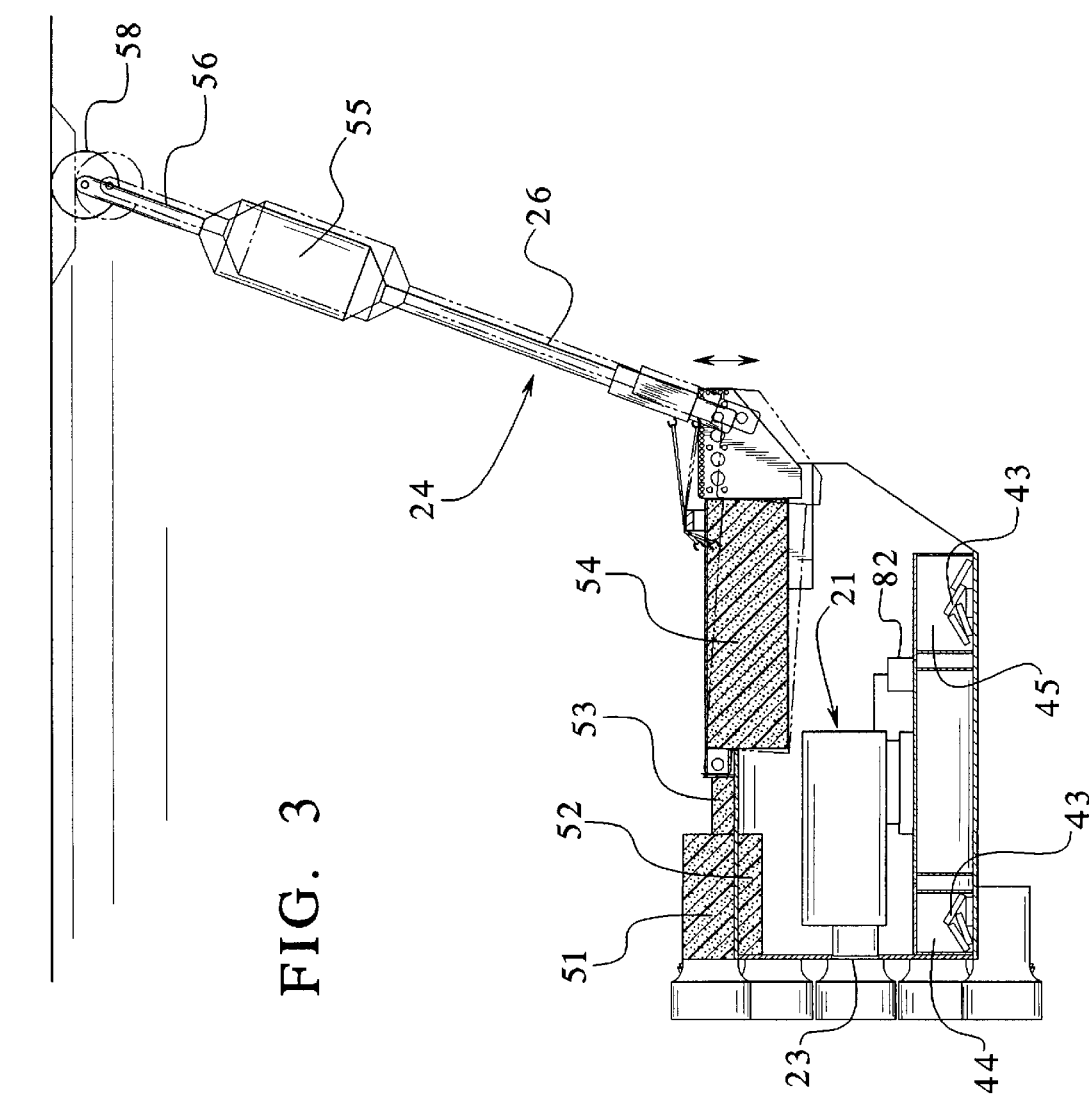
FIG. 3 is a side sectional view of the apparatus shown in FIG. 1.
FIG. 4 is a front elevational view of the apparatus shown in FIG. 1, with the protective cover removed.

Still referring to FIG. 2, a gauge is provided at 38 which enables the diver to adjust the angle of the housing 11 with respect to the axis of the pipeline (not shown). Specifically, the needle 41 hangs freely and the indicating lines 42 will indicate to the diver the angle at which the housing 11 is disposed. Referring to FIG. 3, the buoyancy or angle of inclination may be controlled using weights shown generally at 43 disposed in compartments 44, 45. Additional weight compartments are shown at 46 and 47 in FIG. 4. Foam panels and blocks or other low density materials are shown at 5–54. In addition, a foam buoy 55 is attached to the second section 26 of the two-piece guide leg 24.

The distal end 56 of the second section 26 of the guide leg 24 may be provided with a variety of accessories to assist in the smooth travel of the apparatus through the pipeline. For example, referring to FIG. 2, a skid 57 may be provided or, alternatively, a wheel 58 may be provided as shown in FIG. 3. Still another alternative is to provide a smooth rounded end 59 as shown in FIG. 1. The type of instrument attached to the distal end 56 of the second section 24 will depend upon the conditions inside the pipe and various other alternatives may be considered for specialized conditions, such as the existence of zebra muscles on heavily infested pipe.

Figure 5:
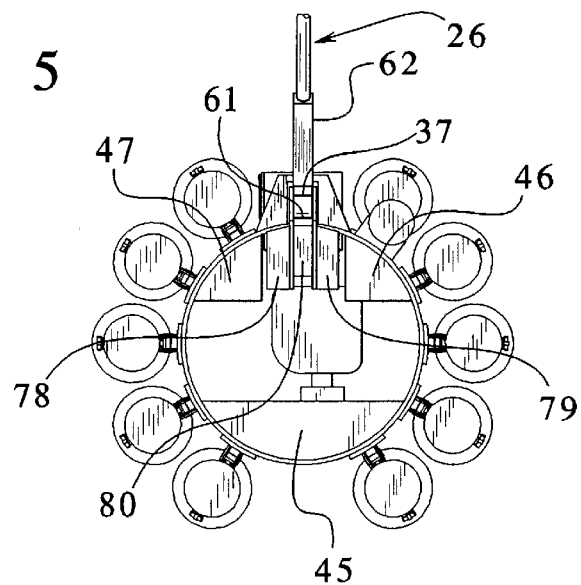
FIG. 5 is a rear elevational view of the apparatus shown FIG. 1.
Figure 6:
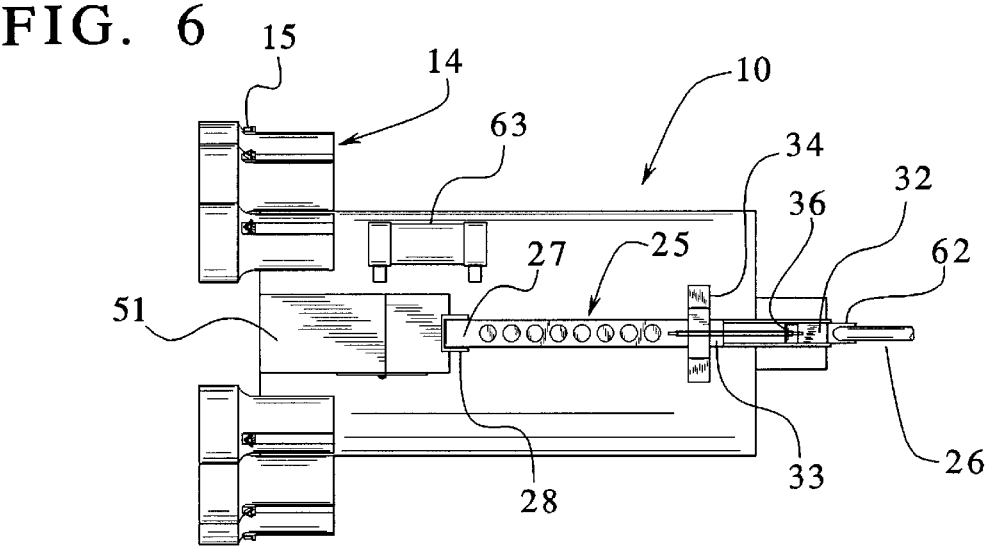
FIG. 6 is a top elevational view of the apparatus shown in FIG. 1.

Turning to FIG. 5, the attachment of the second section 26 to the first section 25 by way of the shaft 61 is illustrated. Also, the second section 26 of the guide leg 24 may include a fitting 62 which includes various sections 26 of various lengths to be attached to the first section 25. In this way, the length of section 26 may be varied for different pipe diameters. If such a fitting 62 is employed, a convenient means for attaching a section 26 to the fitting would be a pin-type connection (not shown). Turning to FIG. 6, a sonic transmitter is shown at 63 which may assist in the location of the apparatus 10 in the event it becomes stuck or lodged in the pipeline during operation.

Figure 7:
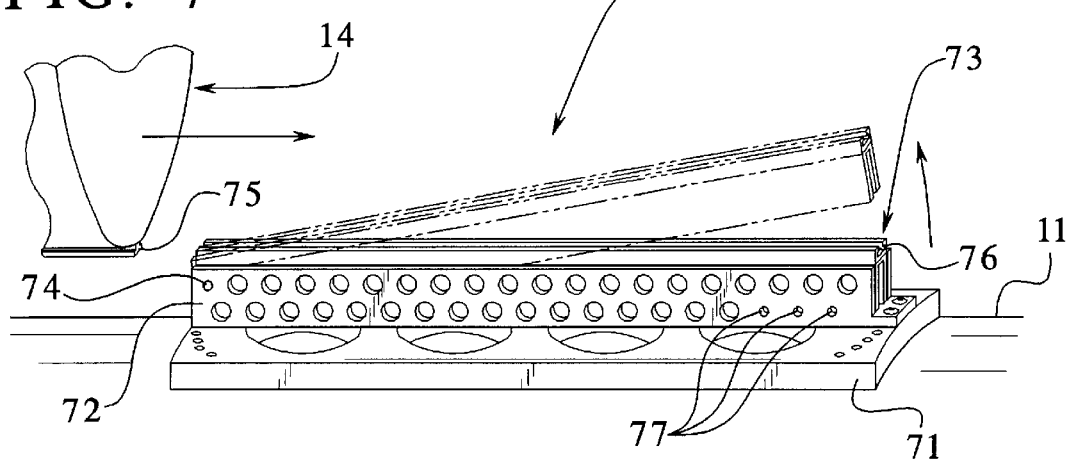
FIG. 7 is an enlarged view of the brackets used to connect the lights to the apparatus shown in FIG. 1.

Turning to FIG. 7, a bracket 70 is shown for attaching the lights 14 to the housing 11. The bracket 70 includes a base 71 that is mounted to the housing. An outer leg 72 is attached to the base which includes a pair of spaced-apart opposing walls between which an inner leg 73 is pivotally mounted with a pin 74. The lights 14 slide onto the inner leg 73 by inserting a tongue 75 disposed on the underside of the light 14 in the groove 76 of the inner leg 73 for a tongue-in-groove-type connection. The angle of the lights 14 with respect to the housing 11 may be adjusted by pivotally moving the inner leg 73 upward. Pins may be inserted into the holes shown at 77 to adjust the desired angle. Nylon ties may be used to hold the lights in place. If inclination of the light in the opposite direction is desired, the base may be removed from the housing 11 and rotated 180°. Returning to FIG. 5, additional foam blocks may be inserted at 78, 79 and 80 for improved buoyancy adjustment.

Buoyancy may be adjusted in a variety of ways by varying the weight distribution in the weight compartments 44–47 and the placement of the foam blocks 51–55 and 78–80. The lights 14 are also adjustable as is the angle of inclination which is primarily adjusted by the two-piece guide leg 24. Specifically, the location of the front stop pin 36 and rear stop pin 37 which enables the angle of the section 26 with respect to the first section 25 to be varied. This, in turn, will vary the inclination of the housing 11 in the pipeline, also depending upon the length of the second section 26 and the diameter of the pipeline. The gauge 38 is useful in determining the angle of inclination. The strength of the elastic member 33 may also be varied in order to adjust the shock absorbing effect of the elastic member 33 which is essentially two-fold. Specifically, the elastic member 33 provides an up/down shock absorbing effect with respect to the first section 25 and a forward/rearward shock absorbing effect with respect to the second section 26.

Any suitable underwater video camera may be utilized for the camera 21. The camera 21 should be securely mounted inside the housing 11 as shown in FIG. 3. The lights shown at 14 are standard scuba lights and include their own separate batteries. Preferably, the camera 21 also includes its own battery. In an embodiment, a timer switch may be used with the camera 21 in order to conserve tape. Specifically, currently-available video tapes are limited to two to six hours in duration. Accordingly, it may be desirable to delay the activation of the video camera for a certain period of time or while the apparatus 10 obtains the appropriate position. A delay mechanism will therefore preserve tape. A delay timer is shown schematically at 82 in FIG. 3.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

What is claimed is:

1. An apparatus for inspecting pipe interiors, the apparatus comprising:

a tubular housing comprising an interior in which a forwardly directed camera is mounted, a front end that is connected to at least one forwardly directed light, a rear end, and an exterior, the exterior comprising an upper portion that is connected to a guide leg, the guide leg comprising a first section and a second section, the first section of the leg being pivotally attached to the upper portion of the exterior of the housing at a bracket disposed at a mid-point of the housing, the first section of the leg extending longitudinally and rearwardly along the exterior of the housing and at least partially through a slot disposed in the rear end of the housing, the second section of the leg being connected to the first section of the leg for limited pivotal movement with respect to the first section and at an upwardly directed angle so that the second section is directed rearwardly and upwardly from the rear end of the housing, the upper portion of the exterior of the housing further comprising a guide through which the first section of the leg passes, the guide limiting the upward and downward pivotal movement of the first section of the leg and substantially limiting the pivotal movement of the first section of the leg to movement within a plane defined by an axis of the housing and the bracket, the first section of the leg comprises a proximal end that is pivotally attached to the housing at the bracket and a distal end that is pivotally attached to the second section of the leg, the distal end of the first section comprising two spaced apart walls, the second section of the leg being disposed between and pivotally attached to the two spaced apart walls, the distal end of the first section further comprising a front pin extending through both walls in front of the second section of the leg and a rear pin extending through both wall behind the second section of the leg, the front and rear pins being spaced apart so that the second section of the leg is able to pivot to a limited extent with respect to the first section of the leg and an elastic member extending between and is attached to the first section of leg and the second section of the leg with the guide and front pin disposed therebetween, the elastic member biasing the second section of the leg against the front pin but permitting pivotal movement of the second leg between the front and rear pins.

2. The apparatus of claim 1 wherein the guide further comprises an upper U-shaped section mounted to the exterior of the housing and a lower U-shaped section mounted to the interior of the housing.

3. The apparatus of claim 1 further comprising a plurality of lights spaced around the front end of the housing, each of said lights being mounted to the housing at a forwardly directed angle with a light bracket that permits the forwardly directed angle of the lights to be adjusted.

4. The apparatus of claim 1 further comprising a plurality of foam segments attached to the housing for buoyancy.

5. The apparatus of claim 1 further comprising a plurality of compartments for accommodating weights for adjusting the buoyancy of the apparatus.

6. The apparatus of claim 1 wherein the front end of the housing comprises a plurality of compartments for accommodating weights for adjusting the buoyancy of the apparatus and the rear end of the housing comprises a plurality of compartments for accommodating weights for adjusting the buoyancy of the apparatus.

7. The apparatus of claim 1 wherein the second section of the leg comprises a distal end, the distal end of the second section of the leg comprising a wheel for reducing friction between the second section of the leg and the pipe.

8. The apparatus of claim 1 wherein the second section of the leg comprises a distal end, the distal end of the second section of the leg comprising an elongated skid for reducing friction between the second section of the leg and the pipe.

9. An apparatus for inspecting pipe interiors, the apparatus comprising:

a tubular housing comprising an interior in which a forwardly directed video camera is mounted, a front end that is connected to at least one forwardly directed light, a rear end, and an exterior, the exterior including an upper section that is connected to a guide leg, the guide leg comprising a first section and a second section, the first section of the leg comprising a proximal end that is pivotally attached to the exterior of the housing at a bracket disposed at a mid-point of the housing, the first section of the leg extending longitudinally and rearwardly along the upper portion of the exterior of the housing and at least partially through a slot disposed in the rear end of the housing, the first section of the leg also extending through a guiding bracket that limits the upward and downward pivotal movement of the first section of the leg with respect to the housing, the guide further comprising an upper U-shaped section mounted to the exterior of the housing and a lower U-shaped section mounted to the interior of the housing, the first section of the leg also comprising a distal end that is pivotally attached to the second section of the leg, the distal end of the first section comprising two spaced apart walls, the second section of the leg being disposed between and pivotally attached to the two spaced apart walls, the distal end of the first section further comprising a front stop pin extending through both walls in front of the second section of the leg and a rear stop pin extending through both wall behind the second section of the leg, the front and rear pins being spaced apart so that the second section of the leg is able to pivot to a limited extent with respect to the first section of the leg, the apparatus further comprising an elastic member that extends between and is attached to the first section of leg and the second section of the leg with the guide and front stop pin disposed therebetween, the elastic member biasing the first section of the leg in an upward position against an upper portion of the guide but permitting downward movement of the first section limited by a lower portion of the guide, the elastic member biasing the second section of the leg in a forward position against the front stop pin but permitting rearward pivotal movement of the second leg between the front and rear pins.

10. The apparatus of claim 9 further comprising a plurality of lights spaced around the front end of the housing, each of said lights being mounted to the housing at a forwardly directed angle with a light bracket that permits the forwardly directed angle of the lights to be adjusted.

11. The apparatus of claim 9 further comprising a plurality of foam segments attached to the housing for buoyancy.

12. The apparatus of claim 9 further comprising a plurality of compartments for accommodating weights for adjusting the buoyancy of the apparatus.

13. The apparatus of claim 9 wherein the second section of the leg comprises a distal end, the distal end of the second section of the leg comprising a wheel for reducing friction between the second section of the leg and the pipe.

14. The apparatus of claim 9 wherein the second section of the leg comprises a distal end, the distal end of the second section of the leg comprising an elongated skid for reducing friction between the second section of the leg and the pipe.

15. A method of inspecting the interior of a pipe while a fluid flows through the pipe, the interior of the pipe having an upper portion and a lower portion, the method comprising the following steps:

placing an apparatus in the pipe, the apparatus comprising a tubular housing comprising an interior in which a forwardly directed video camera is mounted, a front end that is connected to at least one forwardly directed light, a rear end, and an exterior, the exterior including an upper section that is connected to a guide leg, the guide leg comprising a first section and a second section, the first section of the leg comprising a proximal end that is pivotally attached to the exterior of the housing at a bracket disposed at a mid-point of the housing, the first section of the leg extending longitudinally and rearwardly along the upper portion of the exterior of the housing and at least partially through a slot disposed in the rear end of the housing, the first section of the leg also extending through a guiding bracket that limits the upward and downward pivotal movement of the first section of the leg with respect to the housing, the first section of the leg also comprising a distal end that is pivotally attached to the second section of the leg, the distal end of the first section comprising two spaced apart walls, the second section of the leg being disposed between and pivotally attached to the two spaced apart walls, the distal end of the first section further comprising a front stop pin extending through both walls in front of the second section of the leg and a rear stop pin extending through both wall behind the second section of the leg, the front and rear pins being spaced apart so that the second section of the leg is able to pivot to a limited extent with respect to the first section of the leg, the apparatus further comprising an elastic member that extends between and is attached to the first section of leg and the second section of the leg with the guide and front stop pin disposed therebetween, the elastic member biasing the first section of the leg in an upward position against an upper portion of the guide but permitting downward movement of the first section limited by a lower portion of the guide, the elastic member biasing the second section of the leg in a forward position against the front stop pin but permitting rearward pivotal movement of the second leg between the front and rear pins, activating the video camera, permitting the fluid to carry the apparatus along the length of the pipe desired to be inspected, and recording a video of the interior of the pipe as the apparatus is carried through the pipe by the fluid.

\* \* \* \* \*